Figure 1:
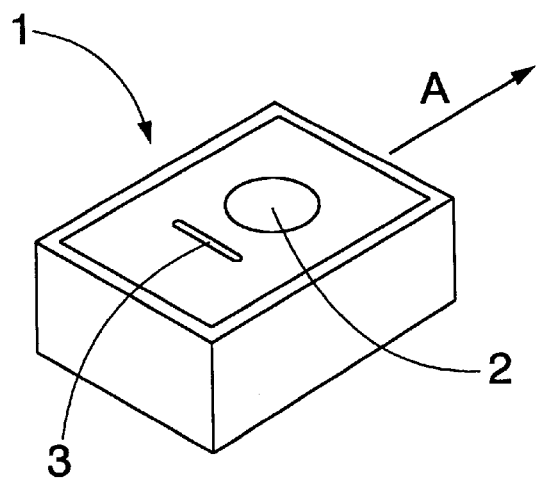

United States Patent [19]

Saikanmäki et al.

[11] Patent Number: 6,091,501
[45] Date of Patent: Jul. 18, 2000

[54] METHOD OF KEEPING MEASURING WINDOW OF MEASURING DEVICE CLEAN, AND MEASURING DEVICE

[75] Inventors: Timo Saikanmäki, Tampere; Hannu Moisio, Kangasala, both of Finland

[73] Assignee: Neles Automation Oy, Helsinki, Finland

[21] Appl. No.: 09/339,429

[22] Filed: Jun. 24, 1999

[30] Foreign Application Priority Data

Jul. 14, 1998 [FI] Finland ..................................... 981607

[51] Int. Cl.7 .......................................................... G01J 3/50
[52] U.S. Cl. ........................... 356/402; 356/429; 359/509
[58] Field of Search ................................... 359/507, 509; 356/402, 429

[56] References Cited

U.S. PATENT DOCUMENTS

| 3,426,200 | 2/1969 | Lehman et al. . |
| 3,662,174 | 5/1972 | McMullen et al. . |
| 4,266,142 | 5/1981 | Crawford ................................. 250/572 |
| 4,602,160 | 7/1986 | Mactaggart . |
| 5,115,342 | 5/1992 | Rowe et al. ............................. 359/509 |
| 5,331,178 | 7/1994 | Fukuda et al. . |

FOREIGN PATENT DOCUMENTS 0 297 271 A2  1/1989  European Pat. Off. .

*Primary Examiner*—F. L. Evans
*Attorney, Agent, or Firm*—Alston & Bird LLP

[57] ABSTRACT

The invention relates to a method of keeping a measuring window of a measuring device clean, and to a measuring device. Gas is blown onto the surface of the measuring window (2) of the measuring device (1). Gas is guided onto the measuring window (2) by a nozzle (3) which is substantially on the same level with the measuring window (2).

18 Claims, 1 Drawing Sheet

METHOD OF KEEPING MEASURING WINDOW OF MEASURING DEVICE CLEAN, AND MEASURING DEVICE

The invention relates to a method of keeping a measuring window of a measuring device clean, the measuring device comprising a substantially planar measuring surface to be arranged close to the product to be measured and a measuring window and a nozzle, the method comprising blowing gas through a nozzle onto the surface of the measuring window.

The invention also relates to a measuring device comprising substantially planar measuring surface to be arranged close to the product to be measured, a measuring window and a nozzle for blowing gas onto the surface of the measuring window.

In the manufacture of paper dirt and dust build up as the paper web is formed and dried, and when the web moves at a high speed in the machine, dirt and dust are spread around the paper machine. Properties of a moving web, such as color, brightness or moisture, are measured by a measuring device which traverses in the transverse direction of the web. The dirt and dust around the paper machine sticks onto the measuring window of the measuring device, which causes distortions in the measurement result.

Measuring windows are typically kept clean by wiping them manually with a cleaning cloth at regular intervals. In that case the measuring device has to be removed from the measuring area for cleaning so that the measuring window can be cleaned. The measuring device and any other measuring devices in the same measuring carriage are out of operation, and thus no measurement results are obtained during cleaning. Furthermore, manual cleaning is laborious and requires service personnel.

EP publication 0 297 271 mentions cleaning of the measuring window by streams of air. However, the publication does not disclose any concrete solution to keeping separate measuring windows clean.

U.S. Pat. No. 4,602,160 discloses a method of keeping the measuring window of a measuring device clean by means of air blowing. Air is blown through an air duct, which covers one edge of the measuring window. Thus the whole surface of the measuring window is not available for measuring, and the measuring beam has to hit the window at a certain angle so that the beam can be detected. Practice has also shown that supply of air in the manner according to the application causes swirling on the surface of the window and makes the current of air rise upwards, and thus air blowing does not keep the window clean efficiently enough. Furthermore, the structure according to the publication is not suitable for measuring paper moving at a high speed because the protrusion resulting from the structure of the air nozzle on the sensor surface against the paper causes problems. The protrusion of the sensor may hit the paper edge when the sensor crosses the paper edge as the measuring carriage crosses the sides of the paper. In addition, wrinkles and protrusions in the paper may touch the sensor, which may cause holes to the paper.

The object of the present invention is to provide a solution which allows to prevent the measuring window from dirtying more efficiently and to avoid the above-mentioned drawbacks.

The method of the invention is characterized in that the nozzle and the measuring window are substantially on the same level with each other and the measuring surface.

The measuring device of the invention is characterized in that the nozzle and the measuring window are substantially on the same level with each other and the measuring surface.

The basic idea of the invention is that gas is blown to keep the measuring window clean and the gas is guided onto the measuring window by a nozzle which is substantially on the same level as the measuring window.

The basic idea of a preferred embodiment is that the edge of the nozzle opening on the side of the measuring window is curved so that a jet of gas turns according to the direction of the surface of the measuring window.

An advantage of the invention is that when the solution of the invention is used, it is not necessary to clean the measuring window manually, or the window has to be cleaned only very seldom. Since the nozzle and the measuring window are substantially on the same level, the whole measuring device is planar and has a uniform surface, i.e. comprises as few points of discontinuity as possible. Thus the measuring device does not hit the paper edges when it crosses the paper edges on the sides of the paper web. It is also easy to prevent the measuring device and the wrinkles and protrusions in the paper from touching each other and thus to prevent holes in the paper. Furthermore, thanks to the even structure, the measuring device can be brought as close to the paper surface as possible.

By providing the edge of the nozzle opening on the side of the measuring window with a curved shape, jets of gas can be made to run in the direction of the surface of the measuring window, and thus dirtying of the window can be prevented, or at least the decrease of the measurement capacity of the measuring device due to impurities can be slowed down.

In this specification the term paper does not only refer to paper but also to paper board.

The invention will be described more closely in the accompanying drawing, in which FIG. 1 is a schematic, axonometric view of a solution according to the invention.

Figure 2:
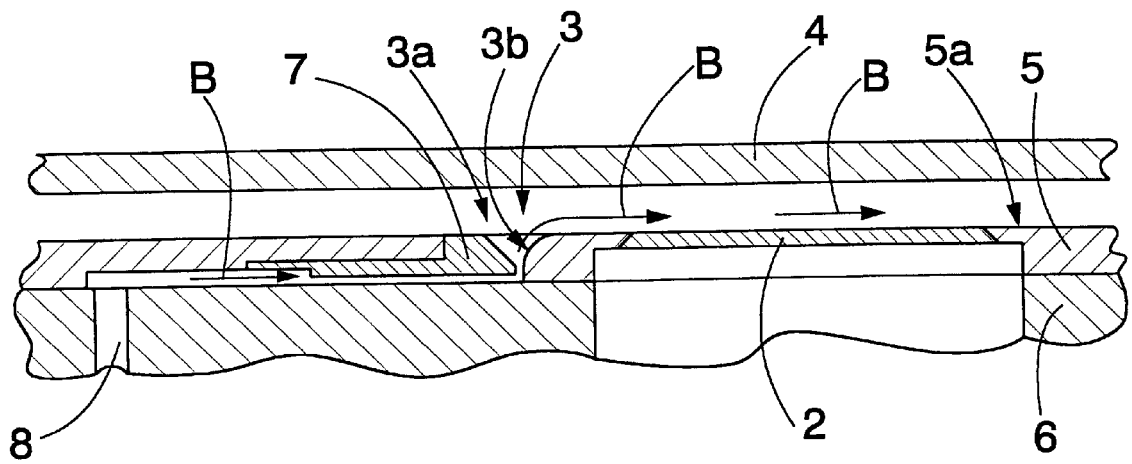
Figure 3:
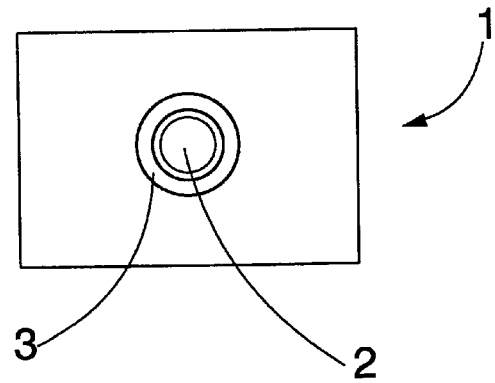

FIG. 2 is a cross-sectional side view of a detail of the solution illustrated in FIG. 1, and FIG. 3 is a schematic top view of another solution according to the invention.

FIG. 1 illustrates a measuring device 1. The measuring device 1 is arranged to measure e.g. color, opacity, moisture, basis weight or another property from a moving web. The structure of the measuring device 1 is completely known per se, and thus it is not explained in greater detail here. A paper web, which is not illustrated in FIG. 1 for the sake of clarity, is arranged to move in the direction of arrow A. The measuring device 1 can be arranged to traverse in a direction substantially transverse to the direction A of the paper web in a manner known per se. The measuring device 1 can be attached e.g. to a measurement frame, which is not illustrated in the figure either for the sake of clarity.

The measuring device 1 comprises a measuring window 2, through which the measurement beam of the measuring device 1 passes. The measuring device also comprises a nozzle 3 which has substantially the same width as the measuring window 2. The nozzle 3 and the measuring window 2 are substantially on the same level. The nozzle 3 is used for guiding a jet of gas onto the measuring window. The nozzle 3 distributes the gas flow over the entire width of the measuring window 2. The gas to be blown is preferably air, but another gas or gas mixture may also be used.

FIG. 2 is a detailed cross-sectional view of the measuring window 2 and the nozzle 3. The measuring window 2 is arranged close to the paper web 4. The measuring window 2 can be attached to the measuring device 1 e.g. by attaching the measuring window to a plate 5 which is attached to the body 6 of the measuring device 1. As is seen in the figure, the plate 5 is provided with a substantially planar measuring surface 5a, which is placed substantially parallel with the surface of the product to be measured. As is also seen in the figure, the measuring window 2 and the nozzle 3 are substantially on the same level both with each other and the measuring surface 5a, which is essential to the invention. The gas to be blown is led along an air feeding channel 8 to a flow channel 9, which is narrower than the air feeding channel 8 and is formed between a flow nozzle 7 and the body 6 of the measuring device. The flow channel 9 ends in a nozzle opening 3a of the nozzle 3. One surface of the nozzle opening 3a is formed by the flow nozzle 7, and the surface of the flow nozzle 3a on the side of the measuring window 2 is formed by a rounded plate 5, which forms a curved guiding surface 3b. Pressurized gas bursting from the flow channel 9 will follow the curved guiding surface 3b and flow in the direction of the surface of the measuring window 2 along the surface of the measuring window 2 according to arrows B. Such a direct air flow cleans the measuring window 2 efficiently.

FIG. 3 illustrates a solution where the nozzle 3 is arranged around an annular measuring window 2. In that case gas is blown onto the measuring window 2 substantially annularly from every direction, and thus the measuring window 2 can be kept clean very well.

The drawing and the description related thereto are only intended to illustrate the inventive concept. The details of the invention may vary within the scope of the claims. Thus with respect to the measuring window 2 the nozzle 3 may be arranged in the direction of the paper web e.g. before the measuring window 2 or on either side of the measuring window.

What is claimed is:

1. A method of keeping a measuring window of a measuring device clean, the measuring device comprising a substantially planar measuring surface to be arranged close to the product to be measured, a substantially planar measuring window and a nozzle, the method comprising blowing gas across the surface of the measuring window through a nozzle, the nozzle and the measuring window being coplanar with each other and the measuring surface.

2. A method according to claim 1, wherein gas is blown substantially over the entire width of the measuring window.

3. A method according to claim 1, wherein gas is blown across the surface of the measuring window annularly from around it.

4. A method according to claim 1, wherein the surface of the nozzle opening of the nozzle is curved on the side of the measuring window so that it turns the gas flow according to the direction of the surface of the measuring window.

5. A method according to claim 1, wherein pressurized gas is supplied to the nozzle opening via a narrow flow channel.

6. A method according to claim 1, wherein the measuring device is used for measuring properties of a moving paper web.

7. A method according to claim 6, wherein the measuring device is used for measuring the color and/or opacity of the paper web.

8. A measuring device comprising a substantially planar measuring surface to be arranged close to the product to be measured, a substantially planar measuring window and a nozzle for blowing gas across the surface of the measuring window, the measuring window and the nozzle being coplanar with each other and the measuring surface.

9. A measuring device according to claim 8, wherein the nozzle is substantially as wide as the measuring window.

10. A measuring device according to claim 8, wherein the nozzle is arranged annularly around the measuring window.

11. A measuring device according to claim 8, wherein the surface of the nozzle opening of the nozzle is curved on the side of the measuring window so that it is arranged to turn the gas flow according to the direction of the surface of the measuring window.

12. A measuring device according to claim 8, wherein the measuring device comprises a narrow flow channel, which is arranged to supply pressurized gas into the nozzle opening.

13. A measuring device according to claim 8, wherein the measuring device is arranged to measure properties of a moving paper web.

14. A measuring device according to claim 13, wherein the measuring device is arranged to measure the color and/or opacity of the paper web.

15. A measuring device comprising a substantially planar measuring surface to be arranged close to the product to be measured, a measuring window and a nozzle arranged annularly around the measuring window for blowing gas across the surface of the measuring window, the measuring window and the nozzle being substantially on the same level with each other and the measuring surface.

16. A measuring device according to claim 15, wherein the surface of the nozzle opening of the nozzle is curved on the side of the measuring window so that it is arranged to turn the gas flow according to the direction of the surface of the measuring window.

17. A measuring device according to claim 15, wherein the measuring device is arranged to measure properties of a moving paper web.

18. A measuring device according to claim 17, wherein the measuring device is arranged to measure the color and/or opacity of the paper web.

\* \* \* \* \*

UNITED STATES PATENT AND TRADEMARK OFFICE
CERTIFICATE OF CORRECTION

PATENT NO.   : 6,091,501
DATED        : July 18, 2000
INVENTOR(S)  : Timo Saikanmaki, et al.

Page 1 of 1

It is certified that error appears in the above-identified patent and that said Letters Patent is hereby corrected as shown below:

Title page,
Item [73] Assignee, should read --Neles Paper Automation Oy, Tampere, Finland--.

Signed and Sealed this

Seventeenth Day of July, 2001

Attest:

NICHOLAS P. GODICI
*Attesting Officer*   *Acting Director of the United States Patent and Trademark Office*